US00PP30592P2

(12) United States Plant Patent
Danziger

(10) Patent No.: US PP30,592 P2
(45) Date of Patent: Jun. 25, 2019

(54) ***LANTANA* PLANT NAMED 'DLANTAN95'**

(50) Latin Name: *Lantana camara*
Varietal Denomination: DLANTAN95

(71) Applicant: Gavriel Danziger, Moshav Mishmar Hashiva (IL)

(72) Inventor: Gavriel Danziger, Moshav Mishmar Hashiva (IL)

(73) Assignee: Danziger "DAN" Flower Farm, Beit Dagan (IL)

( * ) Notice: Subject to any disclaimer, the term of this patent is extended or adjusted under 35 U.S.C. 154(b) by 0 days.

(21) Appl. No.: 15/932,283

(22) Filed: Feb. 16, 2018

(51) Int. Cl.
*A01H 5/02* (2018.01)

(52) U.S. Cl.
USPC ..... Plt./227

(58) Field of Classification Search
USPC ..... Plt./227
See application file for complete search history.

*Primary Examiner* — Susan McCormick Ewoldt
(74) *Attorney, Agent, or Firm* — C. A. Whealy

(57) ABSTRACT

A new and distinct cultivar of *Lantana* plant named 'DLANTAN95', characterized by its compact, upright and mounding plant habit; moderately vigorous growth habit; freely branching growth habit; dense and bushy plant form; dark green-colored leaves; early and freely flowering habit; relatively long flowering period; large inflorescences with large flowers that are initially yellow in color, with development becoming red and yellow and eventually becoming red purple in color; and good garden performance.

2 Drawing Sheets

Botanical designation: *Lantana camara.*
Cultivar denomination: 'DLANTAN95'.

BACKGROUND OF THE INVENTION

The present invention relates to a new and distinct cultivar of *Lantana* plant, botanically known as *Lantana camara* and hereinafter referred to by the name 'DLANTAN95'.

The new *Lantana* plant is a product of a planned breeding program conducted by the Inventor in Moshav Mishmar Hashiva, Israel. The objective of the breeding program is to create new freely-branching *Lantana* plants with early and freely flowering habit and large attractive flowers.

The new *Lantana* plant originated from a self-pollination in August, 2005 in Moshav Mishmar Hashiva, Israel of a proprietary selection of *Lantana camara* identified as code designation LT-7-52, not patented. The new *Lantana* plant was discovered and selected by the Inventor as a single flowering plant from within the progeny of the stated self-pollination in a controlled greenhouse environment in Moshav Mishmar Hashiva, Israel in September, 2005.

Asexual reproduction of the new *Lantana* plant by terminal cuttings in a controlled greenhouse environment in Moshav Mishmar Hashiva, Israel since September, 2005 has shown that the unique features of this new *Lantana* plant are stable and reproduced true to type in successive generations.

SUMMARY OF THE INVENTION

Plants of the new *Lantana* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DLANTAN95'. These characteristics in combination distinguish 'DLANTAN95' as a new and distinct *Lantana* plant:

1. Compact, upright and mounding plant habit.
2. Moderately vigorous growth habit.
3. Freely branching growth habit; dense and bushy plant form.
4. Dark green-colored leaves.
5. Early and freely flowering habit.
6. Relatively long flowering period.
7. Relatively large inflorescences with large flowers that are initially yellow in color, with development becoming red and yellow and eventually becoming red purple in color.
8. Good garden performance.

Plants of the new *Lantana* can be compared to plants of the parent selection. Plants of the new *Lantana* differ primarily from plants of the parent selection in the following characteristics:

1. Plants of the new *Lantana* are shorter than plants of the parent selection.
2. Plants of the new *Lantana* are more freely branching and denser than plants of the parent selection.
3. Plants of the new *Lantana* flower earlier than plants of the parent selection.

Plants of the new *Lantana* can be compared to plants of the *Lantana camara* 'Miss Huff', not patented. In side-by-side comparisons, plants of the new *Lantana* differ from plants of 'Miss Huff' in the following characteristics:

1. Plants of the new *Lantana* are shorter than plants of 'Miss Huff'.
2. Plants of the new *Lantana* flower earlier than plants of 'Miss Huff'.
3. Plants of the new *Lantana* have larger flowers than plants of 'Miss Huff'.

4. Plants of the new *Lantana* and 'Miss Huff' differ in flower color as flowers of plants of 'Miss Huff' are orange and yellow in color.

Plants of the new *Lantana* can be compared to plants of the *Lantana camara* 'DANTAN31', disclosed in U.S. Plant Pat. No. 26,301. In side-by-side comparisons, plants of the new *Lantana* differ from plants of 'DANTAN31' in the following characteristics:

1. Plants of the new *Lantana* are more mounding than plants of 'DANTAN31'.
2. Plants of the new *Lantana* have larger flowers than plants of 'DANTAN31'.
3. Plants of the new *Lantana* and 'DANTAN31' differ in flower color as flowers of plants of 'DANTAN31' are yellow in color.

BRIEF DESCRIPTION OF THE PHOTOGRAPHS

The accompanying colored photographs illustrate the overall appearance of the new *Lantana* plant showing the colors as true as it is reasonably possible to obtain in colored reproductions of this type. Colors in the photographs may differ slightly from the color values cited in the detailed botanical description which accurately describe the colors of the new *Lantana* plant.

The photograph on the first sheet is a side perspective view of a typical flowering plant of 'DLANTAN95' grown in a container.

The photograph on the second sheet is a close-up view of a typical flowering plant of 'DLANTAN95'.

DETAILED BOTANICAL DESCRIPTION

The aforementioned photographs and following observations and measurements describe plants grown during the autumn in 12-cm containers in a greenhouse and finished in an outdoor nursery in Moshav Mishmar Hashiva, Israel and under commercial practices typical of commercial *Lantana* production. During the production of the plants, day temperatures ranged from 22° C. to 32° C. and night temperatures ranged from 22° C. to 28° C. Plants were pinched one time and were eight weeks from planting rooted cuttings when the photographs and the description were taken. In the following description, color references are made to The Royal Horticultural Society Colour Chart, Fifth Edition 2007, except where general terms of ordinary dictionary significance are used.

Botanical classification: *Lantana camara* 'DLANTAN95'.

Parentage:

*Female, or seed, parent*.—Proprietary selection of *Lantana camara* identified as code designation LT-7-52, not patented.

*Male, or pollen, parent*.—Proprietary selection of *Lantana camara* identified as code designation LT-7-52, not patented.

Propagation:

*Type*.—By terminal cuttings.

*Time to initiate roots, summer*.—About one week at temperatures about 25° C.

*Time to produce a rooted young plant, summer*.—About two weeks at temperatures about 25° C.

*Root description*.—Fibrous and fleshy; medium in thickness; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Compact, upright and mounding plant habit; moderately vigorous growth habit; freely branching growth habit; dense and bushy plant form.

*Plant height*.—About 25 cm.

*Plant diameter*.—About 30 cm.

Lateral branch description:

*Branching habit*.—Freely branching habit with potentially two lateral branches developing at every node; pinching enhances lateral branch development.

*Length*.—About 30 cm.

*Diameter*.—About 5 mm to 8 mm.

*Internode length*.—About 2 cm to 4 cm.

*Strength*.—Strong.

*Texture*.—Pubescent, scabrous; longitudinally ridged.

*Color*.—Close to 144A and 144B.

Leaf description:

*Arrangement*.—Opposite, simple.

*Length*.—About 6 cm.

*Width*.—About 4 cm.

*Shape*.—Ovate with deltoid tendencies.

*Apex*.—Acute.

*Base*.—Obtuse.

*Margin*.—Serrulate.

*Texture, upper and lower surfaces*.—Pubescent, scabrous.

*Venation pattern*.—Pinnate, reticulate.

*Color*.—Developing leaves, upper surface: Close to 137A. Developing leaves, lower surface: Close to 146B. Fully expanded leaves, upper surface: Close to 139A; venation, close to 146D. Fully expanded leaves, lower surface: Close to 147B; venation, close to 148D.

*Petioles*.—Length: About 1 cm. Diameter: About 2.5 mm. Strength: Moderately strong, flexible. Texture, upper and lower surfaces: Slightly pubescent, scabrous. Color, upper surface: Close to 146D. Color, lower surface: Close to 148D.

Flower description:

*Flower arrangement and flowering habit*.—Solitary salverform flowers arranged in terminal and axillary hemispherical umbels; flowers face mostly upward or outward; freely flowering habit with about 30 flowers developing per inflorescence and numerous inflorescences developing per plant during the flowering season.

*Natural flowering season*.—Early flowering habit, plants begin flowering about five weeks from planting rooted cuttings; long flowering period, plants of the new *Lantana* flower continuously year round in USDA Hardiness Zones 9 to 11 and from May to September in the cooler zones.

*Flower longevity on the plant*.—About one week; flowers not persistent; inflorescences last about two weeks.

*Fragrance*.—Mildly fragrant; lemony.

*Flowers*.—Appearance: Flared trumpet, corolla fused, four-parted; flowers are sessile. Diameter: About 1.2 cm. Depth (height): About 2 cm.

*Flower buds*.—Length: About 5 mm. Diameter: About 1.5 mm to 2 mm. Shape: Tubular. Color: Close to 61B.

*Corolla*.—Arrangement: Single whorl of four fused petals. Petal lobe length: About 3 mm to 5 mm. Petal lobe width: About 5 mm to 9 mm. Petal lobe shape: Roughly obovate. Petal lobe apex: Rounded and slightly emarginate. Petal margin: Crenate. Petal texture, upper and lower surfaces: Smooth, glabrous. Color: When opening, upper surface: Close to 12A. When opening, lower surface: Close to 46D and 5C. Fully opened, upper surface: Close to 17A and 46C; color becoming closer to 71B with development. Fully opened, lower surface: Close to 51B and 54A; color becoming closer to 72C with development. Throat: Initially, close to 162C; color becoming closer to 186C and 186D with development. Tube: Initially, close to 166D; color becoming closer to 186B with development.

*Calyx*.—Appearance: Tubular calyx with about 20 fused sepals. Length: About 1 cm. Diameter: About 1.5 mm. Sepal shape: Lanceolate. Sepal apex: Pointed. Sepal margin: Entire. Sepal texture, inner and outer surfaces: Pubescent, scabrous. Sepal color, upper and lower surfaces: Close to 141A.

*Pedicels*.—Length: About 3 cm to 5 cm. Diameter: About 1.5 mm to 3 mm. Strength: Strong, flexible. Aspect: About 45° from stem axis. Texture: Pubescent, scabrous. Color: Close to 145A.

*Reproductive organs*.—Stamens: Quantity and arrangement: Four per flower, adnate to floral tube. Filament length: About 2 mm. Filament color: Close to 155A. Anther length: About 1 mm. Anther shape: Narrowly deltoid. Anther color: Close to 7A; color becoming closer to 166A with development. Pollen amount: None observed. Pistils: Quantity: One per flower. Pistil length: About 5 mm. Stigma color: Close to 145D. Style length: About 3 mm. Style color: Close to 145D. Ovary color: Close to 145A. Fruits and seeds: Fruit and seed development have not been observed on plants of the new *Lantana* to date.

Garden performance: Plants of the new *Lantana* have been observed to have good garden performance and to tolerate wind and rain.

Pathogen & pest tolerance: Plants of the new *Lantana* have not been observed to be tolerant to pathogens and pests common to *Lantana* plants to date.

It is claimed:

1. A new and distinct *Lantana* plant named 'DLANTAN95' as illustrated and described.

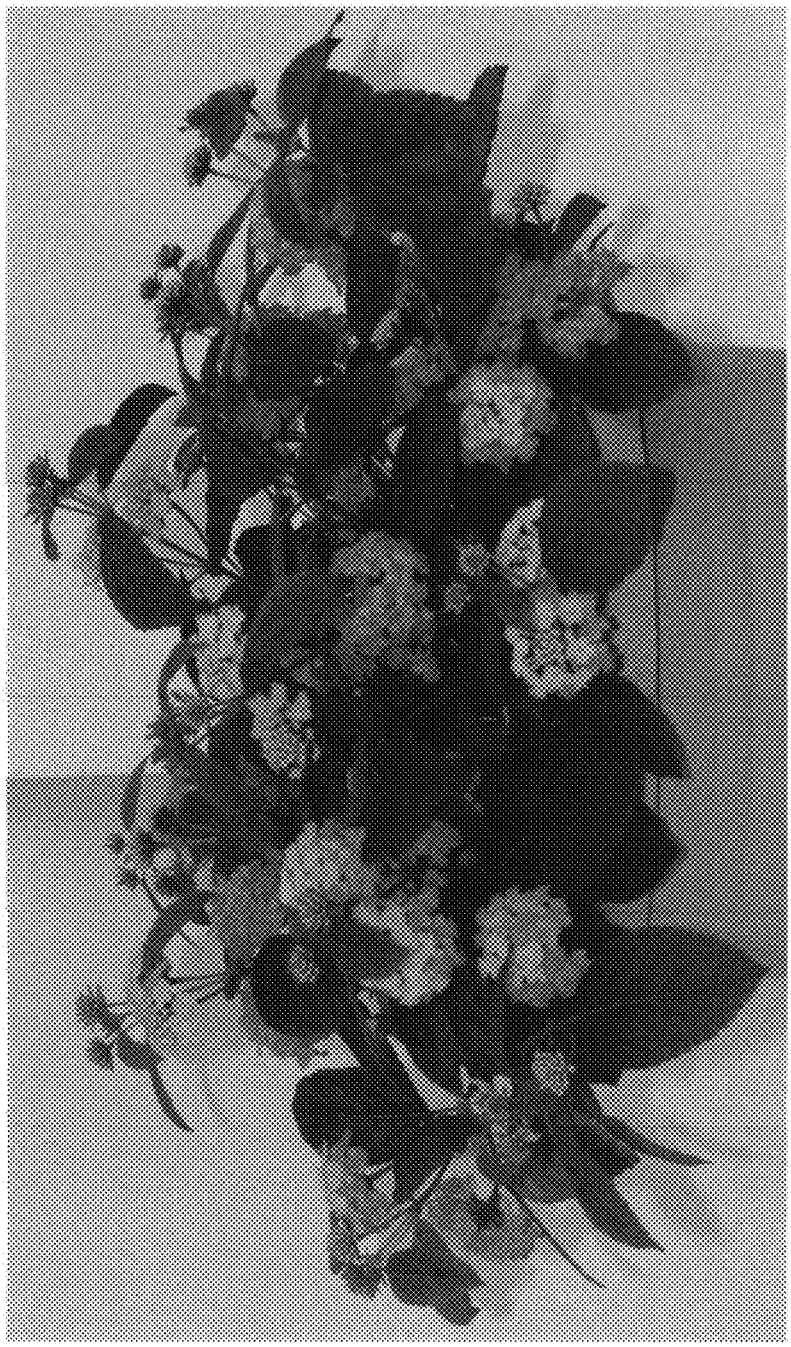

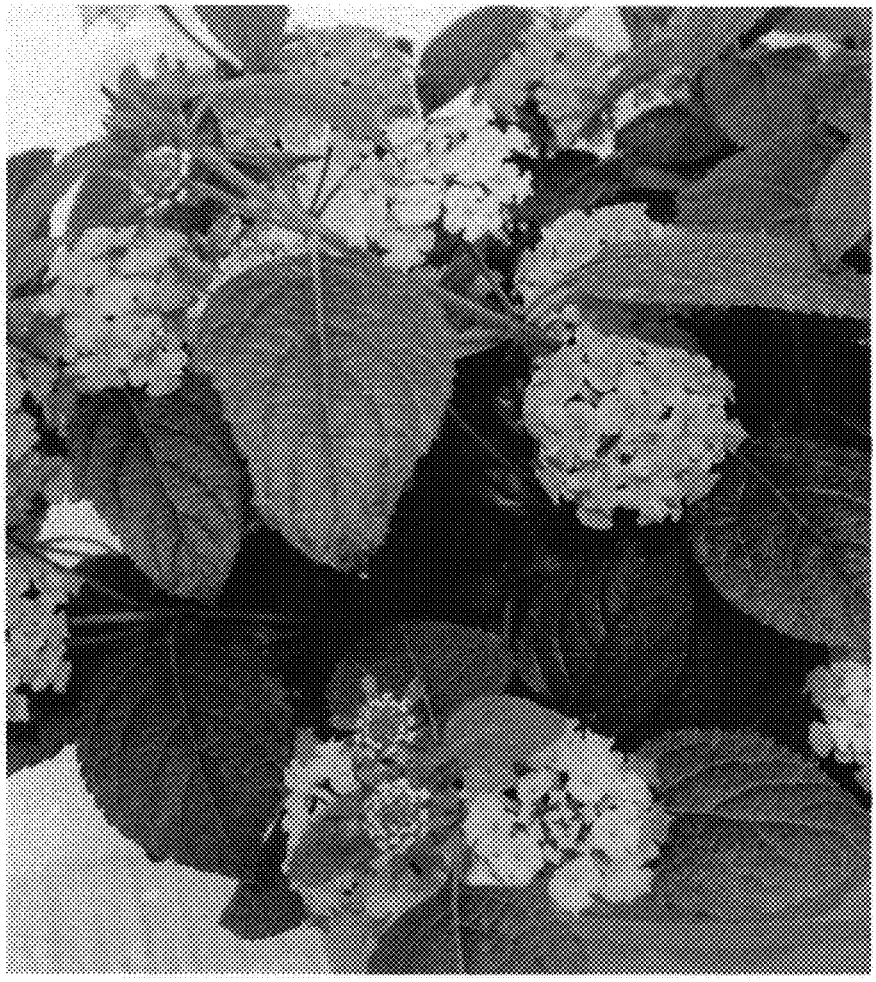

* * * * *